| United States Patent [19] | [11] 3,959,079 |
| --- | --- |
| Mareschi et al. | [45] May 25, 1976 |

[54] INSOLUBILIZATION OF PROTEINS BY CHEMICAL ACTIVATION OF A POLYMERIZED SUPPORT AND CROSSLINKING OF THE PROTEIN TO THE SUPPORT

[75] Inventors: Jean-Pierre Mareschi, Paris; Suzanne Sebesi, Grenoble; Emile Braye, Autorive, all of France

[73] Assignees: L'Air Liquide, Societe Anonyme pour l'Etude et l'Exploitation des Procedes Georges Claude; Orsan, les Produits Organiques du Santerre, both of Paris, France

[22] Filed: June 21, 1974

[21] Appl. No.: 481,750

[30] Foreign Application Priority Data
June 21, 1973 France .............................. 73.22627

[52] U.S. Cl. ................................... 195/63; 195/68; 195/DIG. 11; 260/8; 260/112 R; 210/24
[51] Int. Cl.$^2$ ......................................... C12K 1/00
[58] Field of Search ............... 260/8, 112 R; 195/63, 195/68; 210/24 C

[56] References Cited
UNITED STATES PATENTS

| | | | |
| --- | --- | --- | --- |
| 3,278,392 | 10/1966 | Patchornik............................ | 195/63 |
| 3,645,852 | 2/1972 | Axen et al. ........................... | 195/68 |
| 3,654,083 | 4/1972 | Moelker................................ | 195/63 |
| 3,741,871 | 6/1973 | Weeks et al. ......................... | 195/63 |
| 3,746,622 | 7/1973 | Nishikawa et al.................. | 195/66 R |
| 3,821,084 | 6/1974 | Matthews.............................. | 195/68 |
| 3,836,433 | 9/1974 | Wirth et al............................ | 195/68 |
| 3,853,708 | 12/1974 | Porath et al. ......................... | 195/68 |
| 3,904,478 | 9/1975 | Dean et al. ............................ | 195/63 |

*Primary Examiner*—Donald E. Czaja
*Assistant Examiner*—Edward Woodberry
*Attorney, Agent, or Firm*—Browdy and Neimark

[57] ABSTRACT

Proteins, particularly enzymes, are rendered insoluble in aqueous media by chemical activation of a polymeric support and crosslinking of the active proteins and the support by an inter-molecular bridging agent. The polymer which is used contains free hydroxyl or carboxyl groups and is halogenated and aminated in an organic solvent.

18 Claims, No Drawings

INSOLUBILIZATION OF PROTEINS BY CHEMICAL ACTIVATION OF A POLYMERIZED SUPPORT AND CROSSLINKING OF THE PROTEIN TO THE SUPPORT

FIELD OF THE INVENTION

This invention relates to the insolubilisation of proteins, more particularly but not exclusively of enzymes.

BACKGROUND OF THE INVENTION

Interest in the insolubilisation of enzymes is well-known and an assessment of the methods of preparing enzymes fixed on an insoluble support has been described by several authors, particularly I. H. Silman and E. Katchalski, Ann. Rev. Biochem. (1966) 35, 873, Guilbault (1970) Anal. Chem. 425 334, R. and P. Cautrecasas and collaborators (1971) Ann. Rev. Biochem. 259.

The insolubilisation of enzymes has been carried out by four main types of methods. Firstly, insolubilisation can be achieved by physical adsorption of the enzyme on an inert support or on ion exchanger resins. However, with adsorption methods, there is a permanent danger of desorption of the enzyme occurring and the use of this method remains limited. The ion exchange method was usefully employed for adsorbing an amylocylase on dimethyl aminoethyl cellulose for the first time in 1966. Bernfeld and Wan (Science 142, 678, 1963) were the first to describe the second method for the insolubilisation of enzymes, in which a gel is incorporated in the pores of an ion exchange resin.

Thirdly, fixation of active proteins by covalent bonding on a water-insoluble support is the method which has been most widely used. The enzymatic derivatives which are obtained by this method generally present remarkable properties of resistance to the different denaturation factors. The fixation of the enzyme is effected by the intermediary of functional groups of the enzyme molecule which do not have any effect on the active site. In this type of insolubilisation, it is possible to distinguish between fixation on a previously activated support and fixation by the intervention of a polyfunctional agent. In fixation on an activated support, a functional group of the support is made sufficiently reactive to react with the enzyme. E. Brown (1970), Tetrahedron 25, 2139; Axen (1967) Nature 214, 1302; Porath (1967) Nature 215, 1491; P. Monsan (1971) C. R. Acad. Sci. Paris, 273, pages 33-36 series and French Patent Specification No. 2,133,370 have described the main methods which are based on this principle. In fixation by means of a polyfunctional agent, the latter is first of all fixed on the support and then the enzyme is brought into contact therewith. Examples of polyfunctional agents are given by Kay (1967), Nature 216, 514; H. H. Weetall (1969) Biochim. Biophys. acta 185, 464; and Neurath (1970) FEBS letters 8, 5, 253.

Among the insoluble supports which have been investigated in these different methods, cellulose (a polysaccharide) and its derivatives have frequently been used. Micheel and Envers (Makromol. Chem. 3, 200, 1949) were the first to use Curtins' method for activating the cellulose with an azide and fixing enzymes thereon. Concurrently with this technique of activating the cellulose and its derivatives, there is known the bromoacetyl method of Jagendorpf (Biochem. Biophys. Acta 78, 516, 1963), this implying the formation of a diazo compound as described by Campbell et al (Proc. Nat. Sci. U.S. 37, 575, 1951), that of the carbodiimide described by Weetall (Anal. Biochem. 14, 159–162, 1966) and that of the cyanogen halides described by Axen et al (Nature, 214, 1302-1304).

Among the enzymes which may be fixed by these methods are peroxydases, chymotripsin, trypsin, polynucleotide-phosphorylase, a $\beta$-galactosidase, a lactate dehydrogenase and bromolane.

The fourth method of insolubulisation is characterised by the crosslinking, by covalent bonding, of an enzyme by means of bifunctional agents. This method consists in bonding together several molecules of enzyme (free or adsorbed) by means of a polyfunctional reagent, using one of the techniques published in the works of Silman and Katchalski, Ann. Rev. Biochem. (1966) 35 873; Haynes, (1969) Biochem. Biophys. res. Commun. 36, 235; Selegny (1968) C. R. Acad. Sci. 266, 1431; and French Patent Specification No. 1,604,982.

The methods of chemically fixing enzymes present disadvantages. In particular, the yields are low, the production costs are high and the enzymes are often denatured during the fixation phase.

SUMMARY OF THE INVENTION

We have now found a method of insolubilising active proteins by the combination of chemical activation of the support and crosslinking the proteins to the support by intermolecular bridging agents. The method of chemical activation of the support is a simple method, which permits the fixing of a large number of functional groups capable of operating with enzyme-attachment methods showing the smallest possibility of being denatured. More particularly, the present invention provides a process for rendering a protein insoluble in aqueous media, in which the protein is bonded to a chemically-activated, water-insoluble polymeric support by means of an intermolecular bridging agent, which process comprises halogenating and aminating a polymer containing free hydroxyl or carboxyl groups in an organic solvent by means of a halogenating reagent and a bifunctional aminating reagent to obtain thereby said chemically-activated, water-insoluble polymeric support; and bringing the resultant support into contact with the protein which is to be rendered insoluble and then adding thereto the intermolecular bridging agent.

The water-insoluble, polymeric support can be selected from cellulose and its derivatives, particularly carboxymethyl cellulose; polyacrylic acid, methyl methacrylic acid, the polyamino acids obtained from acidic or basic amino acids and polyvinyl alcohol. The halogenating agent used in the chemical activation of the support can be a thionyl halide, a sulphuryl halide, a phosphorous trihalide or pentahalide, a phosphorous oxyhalide and a halide of p-toluene sulphoxide.

DESCRIPTION OF THE PREFERRED EMBODIMENTS

In one embodiment of the invention, the chemical activation of the support is effected under heat, at a temperature at most equal to 90°C. In this embodiment of the invention, the organic solvent in which the chemical activation reaction takes place is an aromatic hydrocarbon, which optionally may be substituted, for example on the aromatic nucleus; suitable solvents are benzene, the halobenzenes, nitrobenzenes, benzonitriles, toluene and the xylenes.

The organic solvent can be selected from dimethyl formamide, formamide and dimethyl sulphoxide.

In one advantageous embodiment of the invention, the organic solvent contains a small quantity of pyridine, in an amount of a few percent.

In a further embodiment of the invention, the chemical activation reaction is effected in the cold, that is to say at a temperature between 0°C and ambient temperature. Pyridine is the solvent which is preferred when the chemical activation takes place in the cold. However, advantageous variants can be achieved by using mixtures with a high proportion of pyridine and completed either by an aromatic hydrocarbon such as those previously described or by dimethyl formamide, formamide and dimethyl sulphoxide.

The bifunctional aminating agent brought into contact and activated by the halogenation agent can be selected, inter alia, from the group of compounds represented by the formulae:

$NH_2-NH_2$, $NH_2-R_1-NH_2$ and

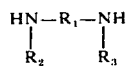

in which $R_1$ is an alkyl radical containing at most 20 carbon atoms optionally substituted by one or more phenyl nuclei and/or a hydroxyalkyl radical containing at most 20 carbon atoms; and in which $R_2$ and $R_3$, which mutually may be the same or different, are lower alkyl radicals or phenyl nuclei.

The active proteins and the chemically activated support are crosslinked by intermolecular bridging agents. It is possible to use polyfunctional agents which are known as bridging agents, such as glutaraldehyde and bis-diazobenzidine. It was found that the bridging agent can also be a dihaloketone, preferably dichloroacetone.

The process of the invention is believed to be applicable to any protein, examples being protease, amylase, lipase, and ribonuclease.

The invention has a wide range of application for the fixation of enzymes on a support, operates under good physiochemical conditions and with good yields. The normal sphere of application is that of enzymatic catalysis and particularly enzymatic reactors.

The improvement in the stability characteristics of the fixed enzymes may permit their use in all those applications where the free proteases are used or where they would be used but do not have a sufficient stability: for example in certain detergent components or in the food industry, such as in the clarification of beer and the elimination from various substrates of undesirable proteins.

The fixation of the amino groups on the support, e.g. on cellulose, may permit particular uses of these modified polysaccharides (e.g. as membranes and anion exchangers). It is thus possible to enlarge the sphere of application of cellulose and to take advantage of the process of the invention with cellulose-based membranes containing active proteins.

Cellulose is very widely used in various chromatographic techniques. Following the treatment according to the invention, it is thus able to form a support which can be used for affinity chromatography after fixation thereonto of an inhibitor specific to the enzyme which is to be isolated.

Examples illustrating the process of the invention and its use are given below in a non-limiting manner.

EXAMPLE 1

Fixation of proteases on cellulose and carboxymethylcellulose

A. Chemical activation of the support and fixation of amino groups.

15 g of cellulose or carboxymethyl cellulose are suspended in 200 ml of benzene or toluene containing about 3% of pyridine and 5 ml of thionyl chloride. The temperature is brought to 80°C for 2 hours and the suspension is left overnight at ambient temperature. The cellulose is then washed with the same solvent and is reintroduced into a further quantity of the solvent, to which is added 5% of ethylene diamine and 3% of pyridine. The mixture is brought to its boiling point and is boiled for at least 2 hours. The mixture is then filtered and the residue washed with the same solvent as was used initially, then washed copiously with water and dried under vacuum. The resultant chemically-activated cellulose or cellulose derivative is coloured to a greater or lesser degree, depending on the solvent used and the degree to which the polysaccharide has been attacked. Elementary analysis shows that the chloride content, $Cl^-$, can reach a maximum of 20% (titration with silver nitrate). Infra-red analysis shows the appearance of

bands, C-NH bands and the existence of the grouping $-NH_2$ on the polysaccharides.

B. Crosslinking of the proteases on the support.

1 g of the activated cellulose or carboxymethyl cellulose, having been subjected to the treatment described above, is brought into contact with 2 ml of 0.02N phosphate buffering agent, at pH 6.8, containing 10 mg/ml of a protease, subtilopeptidase. The mixture is left at 4°C under vacuum until evaporation of the water has occurred, then 2 ml of an approximately 3% glutaraldehyde solution is added. The crosslinked enzyme is thus anchored on the support. Copious washing is then carried out with a solution of sodium bicarbonate and sodium chloride. The residual proteolytic activity of the resultant polysaccharide-protein complex represents a fixation rate of about 0.5% by weight of pure enzyme based on the weight of the support.

EXAMPLE 2

Chemical activation of the support and fixation of amino groups

A. 15 g of cellulose or carboxymethyl cellulose are suspended in 100 ml of pyridine. Stirring takes place for 4 hours at ambient temperature and then the temperature of the suspension is brought to 4°C. 5 ml of thionyl chloride are then added very slowly and the stirring is continued for 3 hours. The mixture is filtered and the residue is thoroughly washed with pyridine and is dried to give the chemically-activated polysaccharide support.

A 20% solution of diaminodiphenyl methane in benzene is prepared. To 100 ml of this solution are slowly added the activated polysaccharide obtained above. Stirring takes place for 2 hours, followed by filtration and copious washing of the residue with benzene. The fibre of polysaccharide carried side chains having at their free ends an amino group; this compound is referred to as derivative 1.

B. Derivative 1 is added very slowly to 100 ml of a solution containing 10 g of dichloroacetone in acetone. Stirring takes place for 4 hours, followed by filtration and thorough washing of the residue with acetone; the acetone is then removed under vacuum. The compound thus obtained is referred to as derivative 2. The polysaccharide support thus obtained carries at the end side chains of Cl⁻ groups, which react with the amine functions.

Derivative 2 is then suspended in 50 ml of 0.04M phosphate buffering agent, pH 7.0, containing 10 mg of purified subtilopeptidase A per ml. The temperature is maintained at 4°C and the suspension is stirred for 48 hours. It is then filtered and the residue washed with several liters of a solution of NaCl and sodium bicarbonate.

The residual proteolytic activity of the resultant polysaccharide-protein complex represents a fixation rate of about 0.5% by weight of pure enzyme based on the weight of the support.

EXAMPLE 3

Application of the protein complex to affinity chromatography.

Purification of α-chymotrypsin by interaction with a specific inhibitor fixed on carboxymethyl cellulose is described below.

10 g of carboxymethyl cellulose with a low degree of substitution are suspended in 50 ml of benzene and 50 ml of pyridine; 5 ml of thionyl chloride is added very slowly, while avoiding any heating. Stirring takes place for 2 hours, followed by filtration and thorough washing of the residue with benzene and pyridine.

12 g of ε-aminocaproic acid are dissolved in 100 ml of water, and the 10 g of previously activated carboxymethyl cellulose are slowly added to this solution. The resulting suspension is stirred for 3 hours, is filtered and the residue thoroughly washed with water. The carboxymethyl cellulose now carries a free carboxyl function originating from the ε-aminocaproic acid. A specific inhibitor of the α-chymotripsin, N-acetyl-D-tryptophane (+), is fixed on the carboxymethyl cellulose at the end of the ε-aminocaproic acid moiety. This fixation is carried out by a condensation method, with the aid of a carbodiimide, between the free ⁻COOH function and the ⁻NH₂ group of the inhibitor.

The carboxymethyl cellulose as thus modified is introduced to a chromatograhic column and balanced by a 0.1M tris buffering agent, pH 8.0. Dissolved in the same buffering agent is a mixture of proteases, including α-chymotripsin, and the buffered solution is introduced into the column. Only the α-chymotripsin is specifically retained by the material in the column. Purification of the α-chymotripsin is thus achieved.

What is claimed is:

1. A process for rendering a protein insoluble in aqueous media, in which the protein is bonded to a chemically-activated, water-insoluble polymeric support by means of an intermolecular bridging agent, which process comprises halogenating and aminating a polymer of cellulose or its derivative containing free hydroxyl or carboxyl groups in an organic solvent by means of a halogenating reagent is selected from the group consisting of thionyl halides, sulphuryl halides, phosphorous trihalides and pentahalides, phosphorous oxyhalides and the halides of p-toluene sulphoxide and a bifunctional aminating reagent selected from the group consisting of compounds represented by the formulae

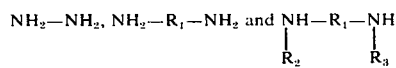

in which $R_1$ is one of an alkyl radical containing at most twenty carbon atoms of which at least one is substituted by a group consisting of a phenyl nucleus and the hydroxyalkyl radicals containing at most 20 carbon atoms, and in which $R_2$ and $R_3$, which mutually may be the same or different, is one of a lower alkyl radical and a phenyl nucleus to obtain thereby said chemically-activated, waterinsoluble polymeric support; and bringing the resultant support into contact with the protein which is to be rendered insoluble and then adding thereto the intermolecular bridging agent.

2. A process according to claim 1, wherein said polymer is carboxymethyl cellulose.

3. A process according to claim 1, wherein chemical activation of said polymer is carried out under heat, at a temperature at most equal to 90°C.

4. A process according to claim 3, wherein the organic solvent used in the chemical activation is an aromatic hydrocarbon.

5. A process according to claim 4, wherein said aromatic hydrocarbon is substituted on the aromatic nucleus.

6. A process according to claim 4, wherein the organic solvent is selected from the group consisting of benzene, the halobenzenes, nitrobenzenes, benzonitriles, toluene and the xylenes.

7. A process according to claim 3, wherein the organic solvent is selected from the group consisting of dimethyl formamide, formamide and dimethyl sulphoxide.

8. A process according to claim 4, wherein the organic solvent contains a small quantity of pyridine.

9. A process according to claim 7, wherein the organic solvent contains a small quantity of pyridine.

10. A process according to claim 1, wherein chemical activation of said polymer is effected in the cold.

11. A process according to claim 10, wherein the organic solvent is pyridine.

12. A process according to claim 10, wherein the organic solvent consists predominantly of pyridine together with a solvent selected from the group consisting of benzene, the halobenzenes, nitrobenzenes, benzonitriles, toluene, the xylenes, dimethyl formamide, formamide and dimethyl sulphoxide.

13. A process according to claim 1, wherein the intermolecular bridging agent is a dihaloketone.

14. A process according to claim 13, wherein the intermolecular bridging agent is dichloroacetone.

15. A process according to claim 1, wherein the intermolecular bridging agent is a polyfunctional agent.

16. A process according to claim 15, wherein said intermolecular bridging agent is selected from glutaraldehyde and bis-diazobenzidine.

17. A process according to claim 1, wherein said protein is an enzyme.

18. A product obtained by the process of claim 1 comprising a water-insoluble, polymeric support cross-linked to a protein by means of an intermolecular bridging agent.

* * * * *